United States Patent [19]

Freeland et al.

[11] Patent Number: 5,269,775
[45] Date of Patent: Dec. 14, 1993

[54] TRISECTION TOPSHEETS FOR DISPOSABLE ABSORBENT ARTICLES AND DISPOSABLE ABSORBENT ARTICLES HAVING SUCH TRISECTION TOPSHEETS

[75] Inventors: Mary E. Freeland, Loveland; Patrick J. Allen, Cincinnati, both of Ohio

[73] Assignee: The Procter & Gamble Company, Cincinnati, Ohio

[21] Appl. No.: 897,689

[22] Filed: Jun. 12, 1992

[51] Int. Cl.⁵ ............................................. A61F 13/15
[52] U.S. Cl. .............................. 604/385.2; 604/385.1; 604/358
[58] Field of Search .................... 604/358, 385.2, 385.1

[56] References Cited

U.S. PATENT DOCUMENTS

| | | | |
|---|---|---|---|
| 4,323,070 | 4/1982 | Ternström et al. | 604/385.2 |
| 4,655,760 | 4/1987 | Morman et al. | 604/385 A |
| 4,834,737 | 5/1989 | Khan | 604/385.2 |
| 4,892,536 | 1/1990 | Desmarais et al. | 604/385.2 |
| 4,990,147 | 2/1991 | Freeland | 604/385.2 |
| 5,037,415 | 8/1991 | Leroy et al. | 604/385.1 |
| 5,037,416 | 8/1991 | Allen et al. | 604/385.1 |
| 5,062,840 | 11/1991 | Holt et al. | 604/385.1 |

FOREIGN PATENT DOCUMENTS

WO92/07533  5/1992  PCT Int'l Appl.
1520740  8/1978  United Kingdom.

*Primary Examiner*—Randall L. Green
*Assistant Examiner*—Rob Clarke
*Attorney, Agent, or Firm*—Larry L. Huston; Fredrick H. Braun

[57] ABSTRACT

A topsheet for use in a disposable absorbent article. The topsheet is divided into three trisections disposed in a particular arrangement along the longitudinal axis of the disposable absorbent article. The front trisection has no elastic extensibility. The central trisection has elastic extensibility in the transverse direction. The rear trisection has elastic extensibility in the longitudinal direction. If desired, the topsheet may be further provided with an aperture for communicating fecal material through the topsheet into a void space in the disposable absorbent article. An exemplary disposable absorbent article is also included in the disclosure.

3 Claims, 7 Drawing Sheets

TRISECTION TOPSHEETS FOR DISPOSABLE ABSORBENT ARTICLES AND DISPOSABLE ABSORBENT ARTICLES HAVING SUCH TRISECTION TOPSHEETS

FIELD OF THE INVENTION

The present invention relates to topsheets for use in disposable absorbent articles, particularly to topsheets for use in disposable absorbent articles which isolate fecal material from the skin of the wearer and to disposable absorbent articles incorporating such topsheets.

BACKGROUND OF THE INVENTION

Disposable absorbent articles are well known in the art. Disposable absorbent articles are worn about the waist to collect and retain exudates from the wearer. These disposable absorbent articles have a liquid pervious topsheet which is worn in contact with the body of the wearer. Bodily exudates, including urine and fecal material, pass through the topsheet to be retained by, in, or near an absorbent core.

Recent advancements in the art include disposable absorbent articles which attempt to isolate fecal material from the skin of the wearer. Such disposable absorbent articles often have a topsheet with an aperture to allow fecal material to pass through the topsheet and which are elasticized to conform closely to the wearer's body, particularly the buttocks.

The balance of the disposable absorbent article may be spaced away from the topsheet, creating a void space for the receipt of fecal material. Examples of such attempts in the art include U.S. Pat. No. 4,834,737 issued May 30, 1989 to Khan and U.S. Pat. No. 5,062,840 issued Nov. 5, 1991 to Holt et al.

Certain attempts in the art only elasticize selected portions of the disposable absorbent article. For example, the topsheet of the disposable absorbent article may be divided into different sections, some of which are elasticized and some of which are not. Examples of such attempts in the art include U.S. Pat. No. 4,655,760 issued Apr. 7, 1987 to Morman et al. and British Patent Application 1,520,740 published Aug. 9, 1978 in the name of Tong.

Other attempts in the art elasticize particular portions of the topsheet of the disposable absorbent article. Such elastication has been achieved through the use of linear elastic strands and elastic panels. Further advances in the art include topsheets which have an elastic modulus that provides a close fitting topsheet that is more comfortable to the wearer. Examples of such attempts in the art include commonly assigned U.S. Pat. No. 4,892,536 issued Jan. 9, 1990 to DesMarais et al., commonly assigned U.S. Pat. No. 4,990,147 issued Feb. 5, 1991 to Freeland, U.S. Pat. No. 5,037,415 issued Aug. 6, 1991 to Leroy et al., and commonly assigned U.S. Pat. No. 5,037,416 issued Aug. 6, 1991 to Allen et al.

However, the prior art attempts to create a topsheet for use in a disposable absorbent article which isolates fecal material from the skin of the wearer do not sufficiently address the competing interest at stake in such a topsheet. For example, some of the aforementioned teachings do not disclose a hole for the transmission of fecal material and therefore cannot address the need to pass the fecal material to a location where it can be isolated from the wearer. Other attempts in the art do not properly balance the need to accommodate the differences in the wearer's anatomy and participation in the excretory functions while the disposable absorbent article is worn. Yet further, the attempts in the art do not address the differences in cleaning the various parts of the wearer's anatomy when the soiled disposable absorbent article is removed and the wearer is to be cleaned.

Clearly, it can be seen that a need exists in the art for a topsheet which properly addresses isolation of fecal material from the skin of the wearer and the comfort of the wearer while the disposable absorbent article is worn. Such a topsheet should further address the differences in the wearer's anatomy which are in contact with the topsheet, and the differences such portions of the anatomy have on the effect of the fit of the disposable absorbent article while it is worn and on the cleaning task after the disposable absorbent article is removed.

BRIEF DESCRIPTION OF THE DRAWINGS

While the Specification concludes with claims particularly pointing out and distinctly claiming the present invention, it is believed the same will be better understood from the following description taken in conjunction with the associated drawings in which like reference numerals represent the same component, analogous components are designated with a prime symbol and:

DETAILED DESCRIPTION OF THE INVENTION

Figure 1:
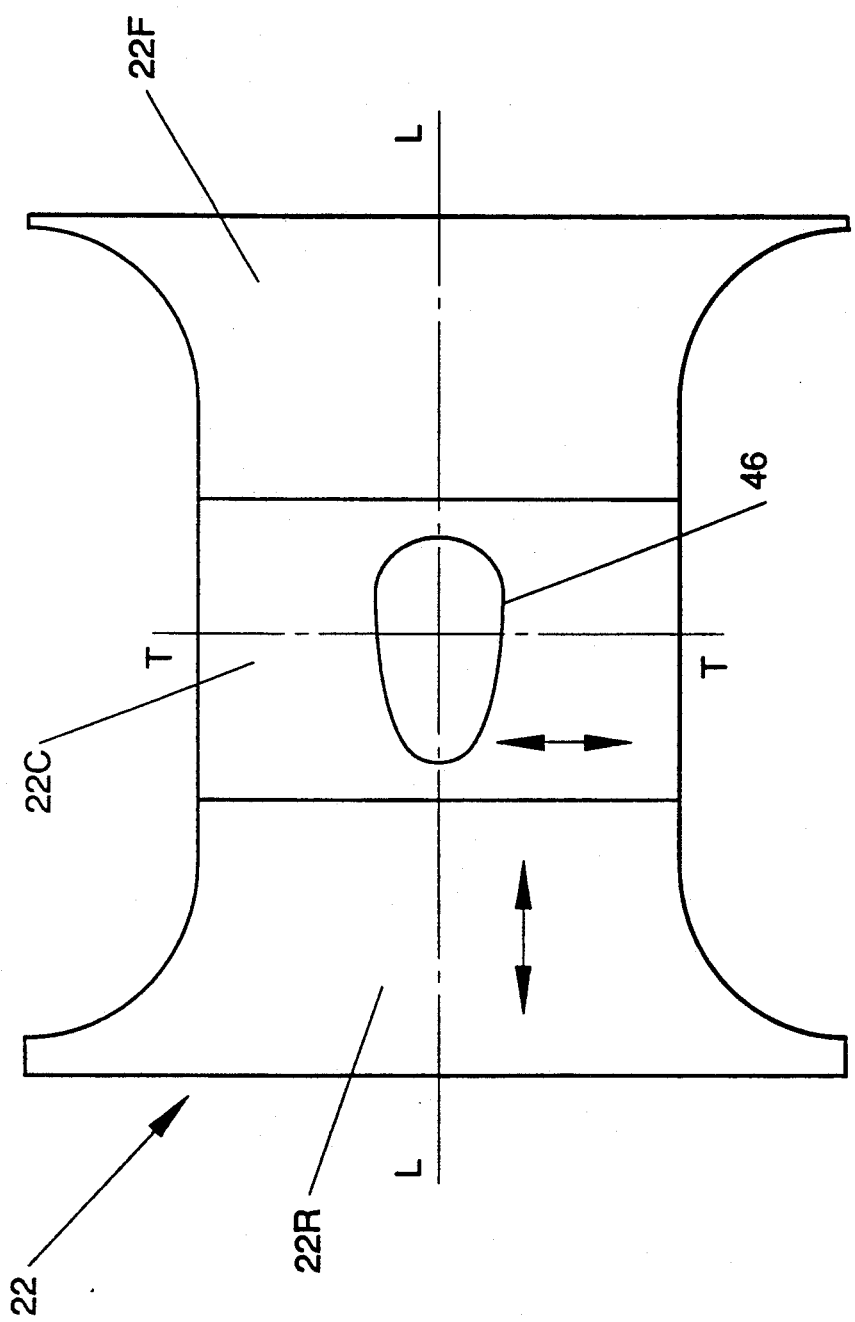
FIG. 1 is a top plan view of a topsheet according to the present invention and having elastic panels extensible in the directions of the arrows.

Referring to FIG. 1, the invention comprises a topsheet 22 which may be utilized in conjunction with a disposable absorbent article 20. As used herein a "topsheet" refers to any liquid pervious facing of a disposable absorbent article 20, such as the one shown in FIG. 2. The topsheet 22 contacts the skin of the wearer while the disposable absorbent article 20 is worn and prevents substantial contact of an absorbent core 26 incorporated into the disposable absorbent article 20 with the skin of the wearer.

As illustrated in FIG. 1, the topsheet 22 according to the present invention is divided into three trisections: a front trisection 22F, a central trisection 22C, and a rear trisection 22R. The rear and central trisections 22R and 22C are elasticized and have different orientations of elasticity. The rear trisection 22R is longitudinally elastically extensible and the central trisection 22C is transversely elastically extensible. The directions of the elastic extensibility are indicated in the figures by the arrows. The front trisection 22F has no elastic extensibility.

The topsheet 22 may, but not necessarily, be provided with an aperture 46 for communicating fecal material through the topsheet 22. Certain advantageous executions of the topsheet 22 according to the present invention, discussed below, work satisfactorily without an aperture 46.

The topsheet 22 is preferably compliant, tactilely pleasant, and nonirritating to the skin of the wearer. Preferably the topsheet 22 is treated to be hydrophilic, to more readily transport body exudates into the core 26 of the disposable absorbent article 20.

Referring back to FIG. 2, a "disposable absorbent article" refers to a garment worn about the body of a wearer which collects body exudates. The disposable absorbent article 20 is intended to be discarded after a single use, and not laundered or otherwise restored (although certain components may be recycled or composted).

A preferred disposable absorbent article 20 according to the present invention comprises a diaper to be worn by an infant. The disposable absorbent article 20 comprises a liquid pervious topsheet 22, a liquid impervious backsheet 24, and an absorbent core 26 intermediate the topsheet 22 and the backsheet 24. The topsheet 22 and the backsheet 24 are at least partially peripherally joined to ensure the core 26 is held in the desired position.

A disposable absorbent article 20 according to the present invention may further comprise elastic leg cuffs and/or barrier leg cuffs to prevent leakage of body exudates through the leg openings of the disposable absorbent article 20 while it is worn. A disposable absorbent article 20 according to the present invention preferably further comprises an elastic waist band to provide for improved fit about the waist of the wearer. A disposable absorbent article 20 according to the present invention may further comprise adhesive tape fasteners 36 juxtaposed with the rear portion 42 of the disposable absorbent article 20 to conveniently secure the disposable absorbent article 20 about the waist of the wearer. For clarity, the elastic leg cuffs, barrier leg cuffs, and elastic waist band are omitted from the figures.

However, if it is desired to incorporate such components into the disposable absorbent article 20, reference is made to commonly assigned U.S. Pat. No. 4,081,301 issued Mar. 28, 1978 to Buell which discloses a method and apparatus for applying elastic strands 54 to a disposable absorbent article 20 to make leg cuffs; commonly assigned U.S. Pat. No. 4,909,803 issued Mar. 20, 1990 to Aziz et al. which shows how to incorporate barrier leg cuffs into a disposable absorbent article 20; commonly assigned U.S. Pat. No. 3,848,594 issued Nov. 19, 1974 to Buell which discloses how to make and incorporate adhesive tape fasteners into a disposable absorbent article 20; and commonly assigned U.S. Pat. No. 4,816,025 issued Mar. 28, 1989 to Foreman which discloses how to make a suitable waist band for a disposable absorbent article 20. The disclosures of these four patents are incorporated herein by reference for the purpose of showing how to advantageously incorporate these optional features into a disposable absorbent article 20 according to the present invention.

Figure 2:
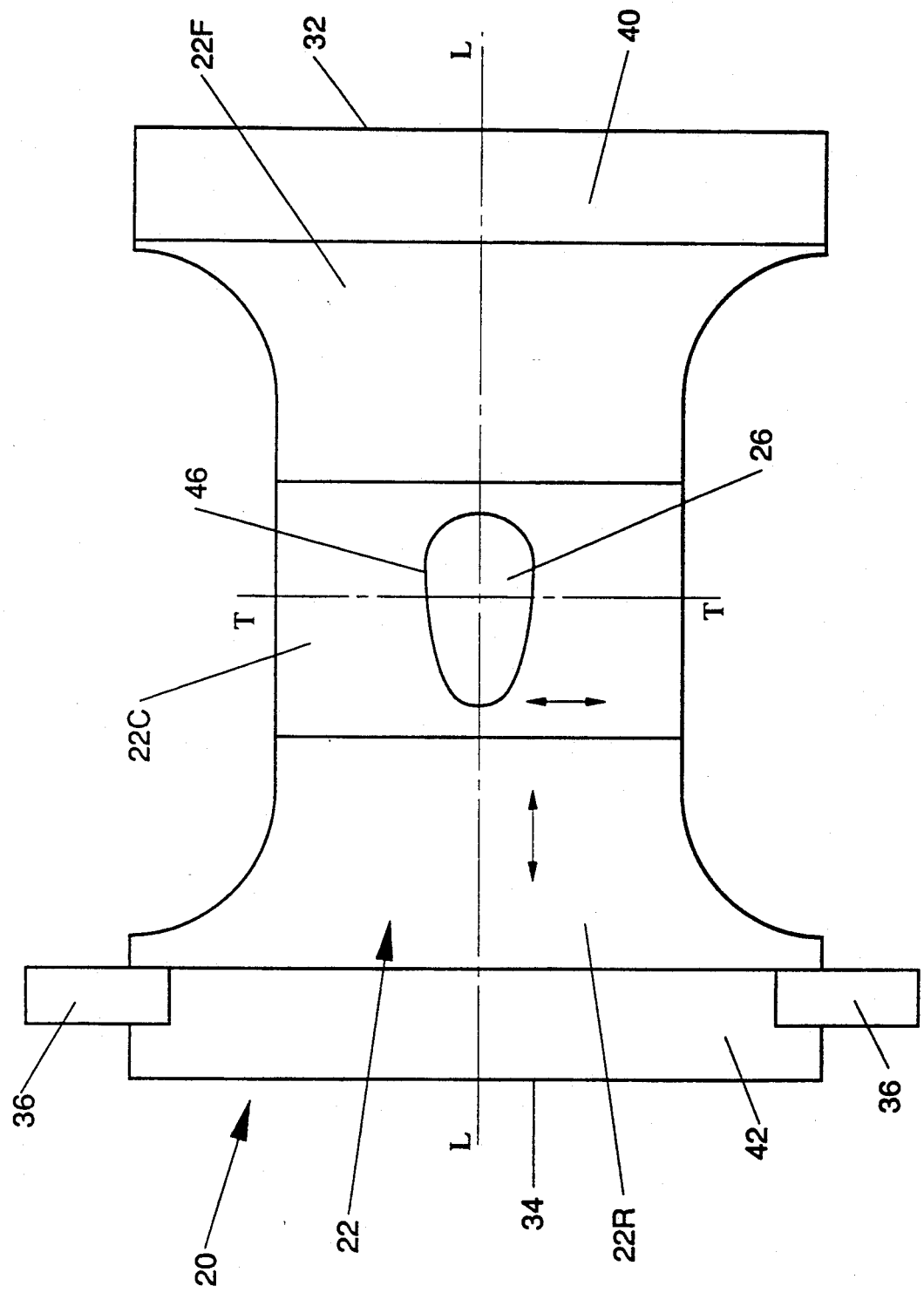
FIG. 2 is a top plan view of a disposable absorbent article incorporating the topsheet of FIG. 1.

FIG. 2 illustrates a disposable absorbent article 20 according to the present invention laid out in a flat state having no elastic induced contraction. The topsheet 22 and the backsheet 24 generally define the periphery of the disposable absorbent article 20. The periphery is the outer perimeter and greatest extent of the disposable absorbent article 20. The periphery comprises a front waist margin 32, a rear waist margin 34, and two longitudinal side margins.

The front waist margin 32 and rear waist margin 34 are those portions of the disposable absorbent article 20 which, when worn, encircle the waist of the wearer and are generally at the highest elevation of the disposable absorbent article 20 when the wearer is in the standing position. The longitudinal side margins are those portions of the disposable absorbent article 20 periphery which connect the front and rear waist margins 32 and 34. The crotch of the disposable absorbent article 20 is that portion of the disposable absorbent article 20 which is disposed between the front waist margin 32 and rear waist margin 34 and which, when worn, is typically between the legs of the wearer.

The core 26 of the disposable absorbent article 20 does not extend into the front waist margin 32 or rear waist margin 34, so that the topsheet 22 and backsheet 24 may be joined and sealed to each other in this area or may be joined and sealed to each other in other areas. Preferably, the front and rear waist margins 32 and 34 longitudinally extend about five percent of the longitudinal dimension of the disposable absorbent article 20 from the edge of the disposable absorbent article 20 towards the transverse axis TT of the disposable absorbent article 20.

As used herein, the "longitudinal" dimension, direction or axis of the disposable absorbent article 20 is that dimension, direction or axis which is aligned front to back with respect to the wearer as the disposable absorbent article 20 is worn. The "transverse" dimension, direction or axis of the disposable absorbent article 20 is generally orthogonal the longitudinal direction and sideways aligned as the disposable absorbent article 20 is worn. The transverse axis TT divides the disposable absorbent article 20 into front and rear portions 40 and 42, corresponding in position to the respective front and rear waist margins 32 and 34. The "Z-direction" is generally orthogonal both the longitudinal and transverse directions, and does not lie within the plane of the disposable absorbent article 20.

The embodiments of the topsheet 22 and disposable absorbent article 20 described herein are suitable for a wearer weighing about 7.3 kilograms to about 12.2 kilograms (16 to 27 pounds). It will be understood that if the topsheet 22 and the disposable absorbent article 20 according to the present invention are intended for use with smaller or larger sized wearers, including adults, the topsheet 22 and the disposable absorbent article 20 will have to be scaled accordingly.

A disposable absorbent article 20 sized to fit the aforementioned range of wearers may be made having a topsheet 22 with a longitudinal dimension of about 43.8 centimeters (17.25 inches) and a backsheet 24 having a longitudinal dimension of about 46.4 centimeters (18.25 inches). The difference in longitudinal dimension between the topsheet 22 and the backsheet 24 foreshortens the topsheet 22 relative to the backsheet 24 creating a void space 52 therebetween, even when a core 26 is interposed between the topsheet 22 and the backsheet 24. The topsheet 22 and backsheet 24 according to the present invention have a transverse dimension at the crotch of about 15.9 centimeters (6.25 inches) and about 21.3 centimeters (8.4 inches) respectively.

The elements of the disposable absorbent article 20 may be assembled in any variety of configurations well known to one skilled in the art. Preferred configurations are described in commonly assigned U.S. Pat. No. 3,860,003 issued Jan. 14, 1975 to Buell, and the aforementioned commonly assigned U.S. Pat. No. 4,909,803 issued Mar. 20, 1990 to Aziz et al., which patents are incorporated herein by reference for the purpose of disclosing well known and preferred disposable absorbent article 20 configurations. In an even more preferred embodiment the configuration of the disposable absorbent article 20 conforms to the teachings of U.S. patent application Ser. No. 07/715,152 filed Jun. 13, 1991 in the name of Buell et al.

Examining the components of the disposable absorbent article 20 in more detail, the topsheet 22 and backsheet 24 are generally coextensive and at least partially peripherally joined together as noted above. As used herein the term "join" refers to the condition where a first member or component is affixed or connected to a second member or component, either directly, or indirectly where the first member or component is affixed or connected to an intermediate member or component which in turn is affixed or connected to the second member or component. The association between the first member or component and the second member or component is intended to remain for the life of the disposable absorbent article 20.

The topsheet 22 and backsheet 24 may be joined by any means well known in the art, such as adhesive bonding or heat sealing. A particularly preferred method of joining the topsheet 22 and backsheet 24 is using hot-melt adhesive such as manufactured by Century Adhesives, Inc. of Columbus, Ohio and marketed as Century 5227 or HL1258 adhesive sold by the H. B. Fuller Company of St. Paul, Minnesota. In a particularly preferred embodiment, adhesive joining is accomplished by longitudinally oriented adhesive bands.

The absorbent core 26 has longitudinal and transverse dimensions generally less than those of the topsheet 22 and the backsheet 24. As used herein the "core" refers to any component of the disposable absorbent article 20 used for absorbing and retaining body exudates. The upper layer 26U and the lower layer 26L of the absorbent core 26 each have opposed major faces and may, if desired, be encased by one or more layers of tissue (not shown), or may be coated with a release agent to reduce friction against the fecal material.

The tissue layer, if present, improves the tensile strength of the absorbent core 26 and reduces its tendency to split or clump when wetted. The tissue may further improve transverse wicking of fluids and more evenly distribute absorbed liquids throughout the absorbent core 26. A tissue layer having a basis weight of approximately 16 grams per square meter (10 pounds per 3,000 square feet) and an air permeability of approximately 30 cubic meters per minute per square meter (100 cubic feet per minute per square foot) and a differential pressure of 13 millimeters of water (0.5 inch of water) has been found to work well. Alternatively, the topsheet 22 may separately or also wrap around the core 26.

The absorbent core 26 may be made from a variety of commonly used materials such as comminuted wood pulp, typically referred to as air felt. If desired, the absorbent core 26 may further contain absorbent gelling materials as is commonly used in the art. In particular, the absorbent core 26 may be made in accordance with the teachings of commonly assigned U.S. Pat. No. 4,610,678 issued Sep. 9, 1986 to Weisman et al., which patent is incorporated herein by reference for the purpose of showing how to make an absorbent core 26 suitable for use with the present invention. Absorbent gelling materials made in accordance with commonly assigned U.S. Pat. No. 32,649 issued Apr. 19, 1988 to Brandt et al. have been found suitable for use in a disposable absorbent article 20 according to the present invention.

If desired, in a particularly preferred embodiment the absorbent core 26 may have discrete storage and acquisition zones. The storage zone has a higher average density and higher average basis weight than the acquisition zone, so that the acquisition zone may effectively and efficiently acquire rapidly discharged liquids and transport the same to the storage zone for long term containment. Such a core 26 may be made in accordance with the teachings of commonly assigned U.S. Pat. No. 4,834,735 issued May 30, 1989 to Alemany et al., which patent is incorporated herein by reference for the purpose of showing how to make a particularly preferred lower layer 26L of the core 26. A very suitable core 26 material is a fibrous absorbent gelling material such as is sold under the tradename Fibersorb by the Atlantic Richfield Company of Los Angeles, California.

The core 26 may be adhesively joined to the topsheet 22 and/or backsheet 24 respectively by any attachment means well known in the art. A particularly preferred attachment means is adhesive spirals and longitudinal and transverse bands of adhesive. Particularly preferred types of adhesive are manufactured by Century Adhesives, Inc. of Columbus, Ohio as Century 5227, HL-1258 Adhesive sold by the H. B. Fuller Company of St. Paul, Minnesota and XPO-9-035 adhesive manufactured by the Minnesota Mining and Manufacturing Company of St. Paul, Minnesota.

The backsheet 24 is impervious to fluids, such as urine, and prevents fluids absorbed by and contained in the absorbent core from wetting undergarments, clothing, and bedding. As used herein the "backsheet" refers to any barrier disposed outwardly of the core 26 as the disposable absorbent article 20 is worn and which contains absorbed liquids within the disposable absorbent article 20. Preferably the backsheet 24 is flexible, compliant, and readily conforms to the general shape and contour of the wearer's body.

The backsheet 24 may be a polyolefinic film, such as polyethylene, having a thickness of about 0.01 millimeters to about 0.051 millimeters (0.005 to 0.002 inches). If desired, the backsheet 24 may be embossed or matte finished to provide a cloth-like appearance or provided with passages to permit vapor escape. A suitable backsheet 24 can be made from a blend of about 45 to about 90 percent linear low density polyethylene and about 10 to 55 percent polypropylene. Exemplary backsheet 24 films are sold by Tredegar Industries, Inc. of Terre Haute, Indiana under the designation RR8220 blend for blown films and RR5475 blend for cast films.

Figure 3:
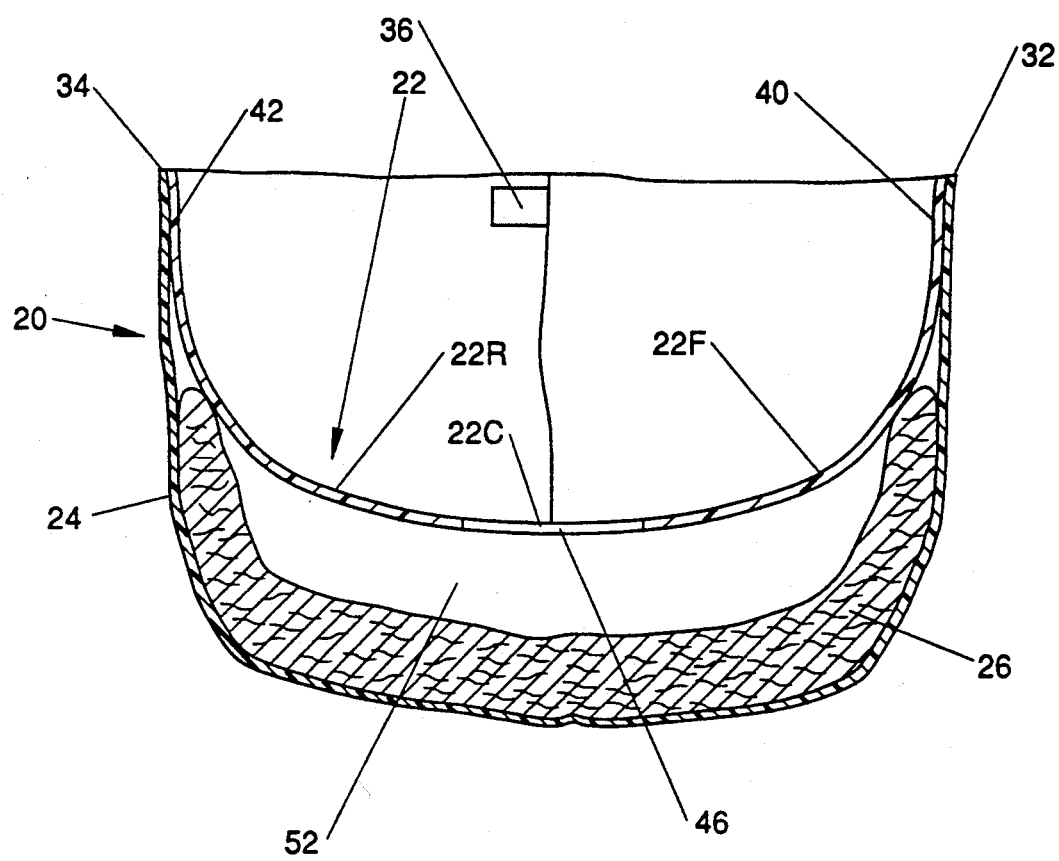
FIG. 3 is a longitudinal vertical sectional view of the disposable absorbent article of FIG. 2 shown in an in use configuration.

Referring to FIG. 3, preferably the topsheet is longitudinally foreshortened relative to the core 26 and/or backsheet 24 of the disposable absorbent article 20. This arrangement creates a void space 52 between the core 26 and the backsheet 24.

The pervious topsheet 22 further comprises an aperture 46 transversely centered on the longitudinal axis LL. The aperture 46 provides a passageway for the communication of fecal material from the anal opening through the topsheet 22 into the void space 52. Preferably absorbent gelling materials present in the core 26 are not registered with the aperture 46, so that gell-blocking does not occur when large volume urine loading occurs.

The aperture 46 may be of any shape desired with a particularly preferred shape being an oval having a longitudinal dimension of about 5.1 centimeters (2.0 inches) and a transverse dimension of about 3.8 centimeters (1.5 inches). The rearwardmost edge of the aperture 46 is disposed at least about 15.2 centimeters (6.0 inches), and preferably about 17.8 centimeters (7.0 inches) from the rear waist margin 34 of the disposable absorbent article 20 while it is worn.

A suitable topsheet 22 may be manufactured from materials such as porous foams, apertured plastic films, natural fibers (e.g. wood fibers or cotton fibers), synthetic fibers (e.g. polyester or polypropylene fibers) or a combination of the foregoing. A particularly preferred topsheet 22 comprises polypropylene fibers having a denier of about 2.2 and a length of about 15.9 millimeters (0.62 inches). The topsheet 22 may be manufactured according to a number of techniques and may be woven, nonwoven, spunbonded, carded, etc.

A particularly preferred topsheet 22 is carded and thermally bonded and has a weight of about 18 to about 25 grams per square meter, a minimum dry tensile strength of about 400 grams per centimeter taken in the machine direction and a minimum wet tensile strength of at least about 55 grams per square centimeter taken in the cross machine direction. A suitable topsheet 22 is marketed by Veratec, Inc., Division of International Paper Company of Walpole, Massachusetts under the designation P-8.

Referring back to FIG. 1, the topsheet 22 according to the present invention is divided into three trisections disposed in a particular arrangement along the longitudinal axis LL of the disposable absorbent article 20.

The rear trisection 22R has a means for elastically longitudinally contracting the rear trisection 22R. The central trisection 22C has a means for elastically transversely contracting the central trisection 22C. The front trisection 22F has no means for providing elasticity to the front trisection 22F.

The rear and central trisections 22R and 22C have longitudinal and transverse elastic extensibility, respectively and as illustrated by the arrows, and may have such extensibility imparted by generally two-dimensional elastic panels. As used herein "panels" are considered to be two dimensional if they have principal dimensions lying within the plane of the topsheet 22 and a relatively small thickness in the Z-direction. Of course, it is to be recognized that the panels are only conceptually two dimensional because of this thickness in the Z-direction. However, such thickness in the Z-direction is small enough to be insignificant relative to the longitudinal and transverse dimensions of the front, rear, and central trisections 22F, 22R, and 22C of the topsheet 22.

Particularly preferred elastic trisections 22R and 22C of the topsheet 22 according to the present invention have an elongation greater than 50 percent and less than 350 percent under a tensile load of about 800 grams per centimeter of width. Such an elongation at this tensile loading provides a topsheet 22 which is very comfortable to the wearer, as noted above. Such a topsheet 22 may be made in accordance with the aforementioned commonly assigned U.S. Pat. No. 5,037,416 issued to Allen et al., which patent is incorporated herein by reference for the purpose of showing how to make a material particularly suitable for the rear trisection 22R and the central trisection 22C of the topsheet 22 according to the present invention.

The longitudinally elastically extensible rear trisection 22R provides for close conformance of the topsheet 22 to the buttocks of the wearer. As used herein, a component is considered to be "elastically extensible in the longitudinal direction," and to provide longitudinal elastic extensibility to another component and in the longitudinal direction, if such component has a principal axis of elastic elongation oriented within ±45 degrees of the longitudinal axis LL.

This longitudinal elastic extensibility allows the void space 52 to be present in the area of the disposable absorbent article 20 juxtaposed with the rear waist margin 34 in order to advantageously receive fecal material. It is important that the rear trisection 22R not sag or festoon into the void space 52, otherwise transport and migration of fecal material away from the aperture 46 may be inhibited, causing less fecal material to pass through the aperture 46 and instead remain in contact with the skin of the wearer subjacent or in the region of the central trisection 22C.

For the embodiments described herein, the rear trisection 22R may have a longitudinal dimension, taken from the rear waist margin 34 to the border with the central trisection 22C of about 20.3±1.9 centimeters (8±0.75 inches). Such a rear trisection 22R may be made in the form of a two-dimensional panel and according to the teachings of commonly assigned U.S. Pat. No. 5,037,416 issued to Allen et al. as discussed above and for the reasons noted above.

The central trisection 22C of the topsheet 22 according to the present invention is elastically extensible in the transverse direction. As used herein a component is considered to be "elastically extensible in the transverse direction," and to provide transverse elastic extensibility to another component and in the transverse direction, if such component has a principal axis of elastic elongation oriented within ±45 degrees of the transverse axis TT.

This arrangement provides the advantage that contraction of the disposable absorbent article 20 occurs in the crotch portion, intermediate the front waist margin 32 and the rear waist margin 34. Such transverse contraction provides for shaping of the disposable absorbent article 20 in the familiar hourglass to more comfortably fit the wearer while the disposable absorbent article 20 is in use.

However, the transverse contraction may tend to close the aperture 46. Therefore, care must be taken that too much contraction is not imparted to the central trisection 22C of the topsheet 22. If too much contraction is imparted and the aperture 46 does not remain open, fecal material may not pass through the aperture 46 into the void space 52. If the fecal material should remain on the topsheet 22, it will remain in contact with the skin of the wearer causing the irritation discussed above and complicating the task of cleaning the wearer.

Such a central trisection 22C may be made in the form of a two dimensional panel and according to the teachings of commonly assigned U.S. Pat. No. 5,037,416, issued to Allen et al. as discussed above and for the reasons noted above. For the embodiments described herein, the central trisection 22C may have a longitudinal dimension, between the border of the rear trisection 22R and the border of the front trisection 22F of about 8.1±1.9 centimeters (3.2±0.75 inches). Preferably, the longitudinal dimension of the central trisection 22C is sufficient to encompass the entire aperture 46.

The front trisection 22F may be provided without any elastic extensibility whatsoever. This arrangement provides the advantages of economization of materials, as well as increased perviousness for the acquisition of liquids, such as urine. Additionally, a front trisection 22F which is not elastically extensible will conform less closely to the wearer and more comfortably accommodate the genitalia, particularly of the male wearer.

For the embodiments described herein, the front trisection 22F may have a longitudinal dimension between the front waist margin 32 and the border of the central trisection 22C of about 16.8±1.9 centimeters (6.6±0.75 inches). Alternatively, the front trisection 22F may have a greater longitudinal dimension than the rear trisection 22R.

Figure 4:
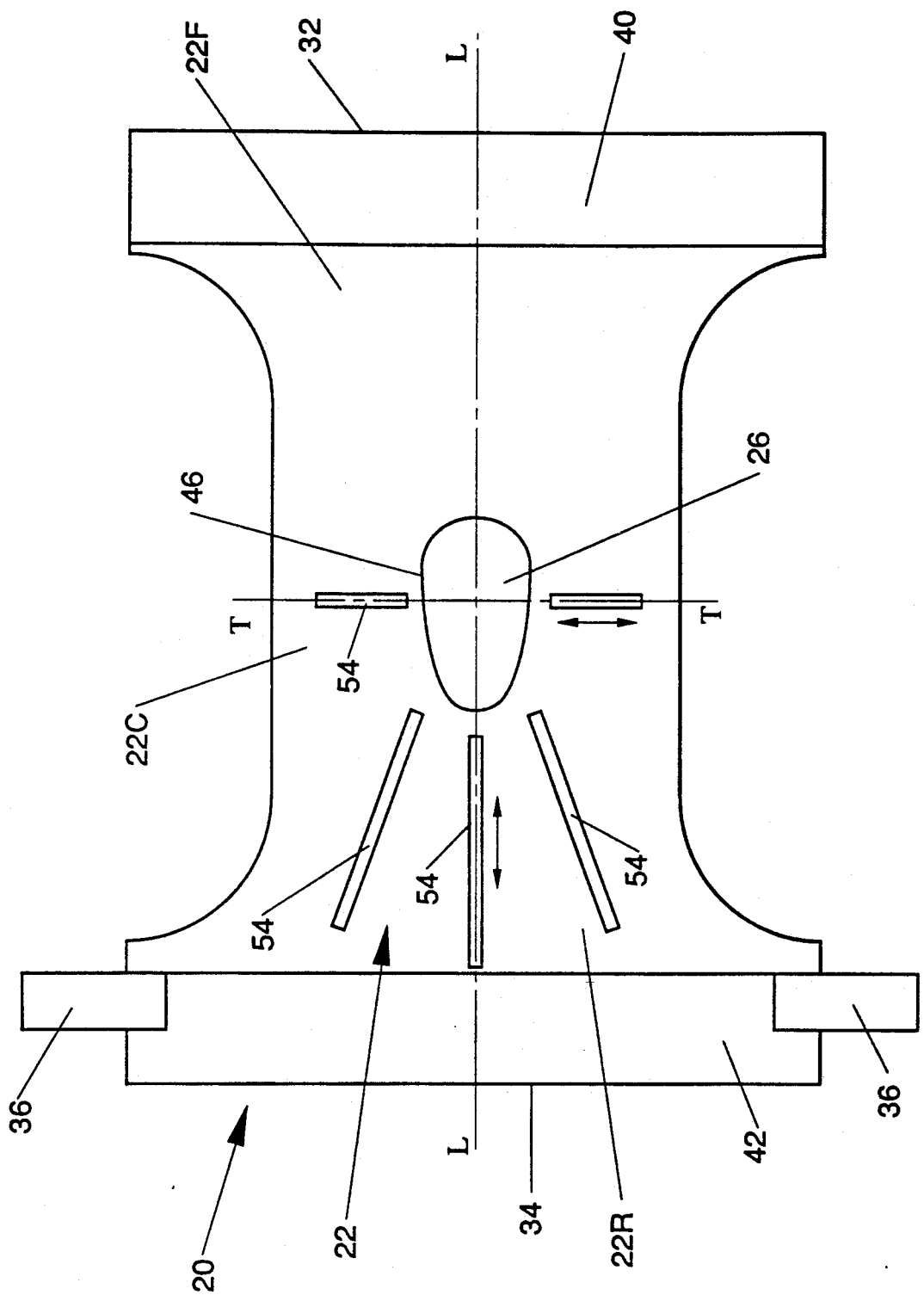
FIG. 4 is a top plan view of an alternative embodiment of a disposable absorbent article having a topsheet according to the present invention with linear elastic strands extensible in the directions of the arrows.

Referring to FIG. 4, in a variant embodiment the elasticity may be applied to the rear trisection 22R and/or the central trisection 22C of the topsheet 22 by linear elastic strands 54, rather than by two dimensional panels. The elastic strands 54 are oriented longitudinally, in the rear trisection 22R and are preferably longitudinally parallel. The elastic strands 54 are longitudinally oriented in the rear trisection 22R, and are preferably parallel the longitudinal axis LL, although, as illustrated, some derivation from the transverse direction can be tolerated.

In such an arrangement, the rear trisection 22R may have one elastic strand 54 coincident the longitudinal axis LL, so that the rear trisection 22R is pulled into the gluteal groove of the wearer. Outboard elastic strands 54, preferably symmetrical about the longitudinal axis LL, may be provided as desired in the rear trisection 22R. If the elastic strands 54 in the rear trisection 22R deviate from the transverse direction, preferably the elastic strands 54 diverge towards the rear waist margin 34 so that the rear trisection 22R may more accurately fit and conform the buttocks of the wearer.

The central trisection 22C may have elastic strands 54 parallel the transverse TT and centered on the aperture 46, or, may have transversely oriented elastic strands 54 on either side of the transverse axis TT and otherwise not centered on the aperture 46.

It is not necessary that the longitudinally oriented elastic strands 54 in the rear trisection 22R or the transversely oriented elastic strands 54 in the central trisection 22C be disposed in any particular arrangement. It is only important that the rear trisection 22R have a means for longitudinally contracting the rear trisection 22R and the central trisection 22C have a means for transversely contracting the central trisection 22C.

If it is desired to incorporate elastic strands 54 into a topsheet 22 or disposable absorbent article 20 according to the present invention, such elastic strands 54 may be incorporated according to the teachings of the aforementioned and commonly assigned U.S. Pat. No. 4,892,536 issued Jan. 9, 1990 to DesMarais et al., which patent is incorporated herein by reference for the purpose of showing a particularly preferred way to incorporate elastic strands 54 into a topsheet 22 and disposable absorbent article 20 according to the present invention. In a particularly preferred embodiment, the elastic strands 54 have elastic extensibility as described in the aforementioned and commonly assigned U.S. Pat. No. 5,037,416 issued Aug. 6, 1991, to Allen et al., which patent is incorporated herein by reference for the purpose of showing a preferred construction of the elastic strands 54.

Figure 5:
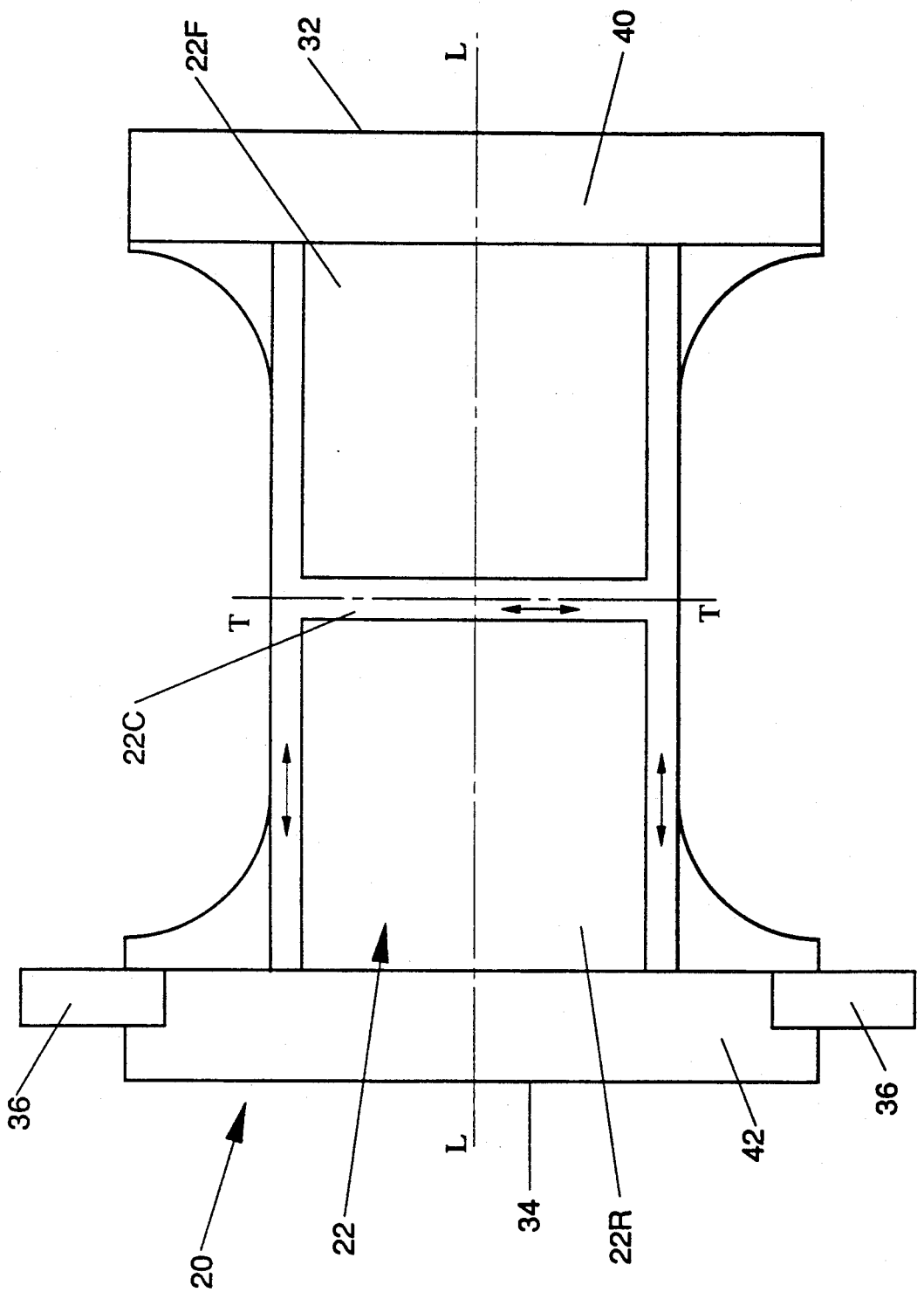
FIG. 5 is a top plan view of a disposable absorbent article according to the present invention having no aperture, and a central trisection which longitudinally extends into the front and rear trisections which trisections are extensible in the directions of the arrows.

Referring to FIG. 5, in yet another embodiment the individual trisections 22F, 22C and 22R may longitudinally overlap. For example, the central trisection 22C may longitudinally extend into the areas occupied by either or both the front trisection 22F and/or the rear trisection 22R. This arrangement yields a central trisection 22C having a somewhat H-shaped configuration.

Figure 6:
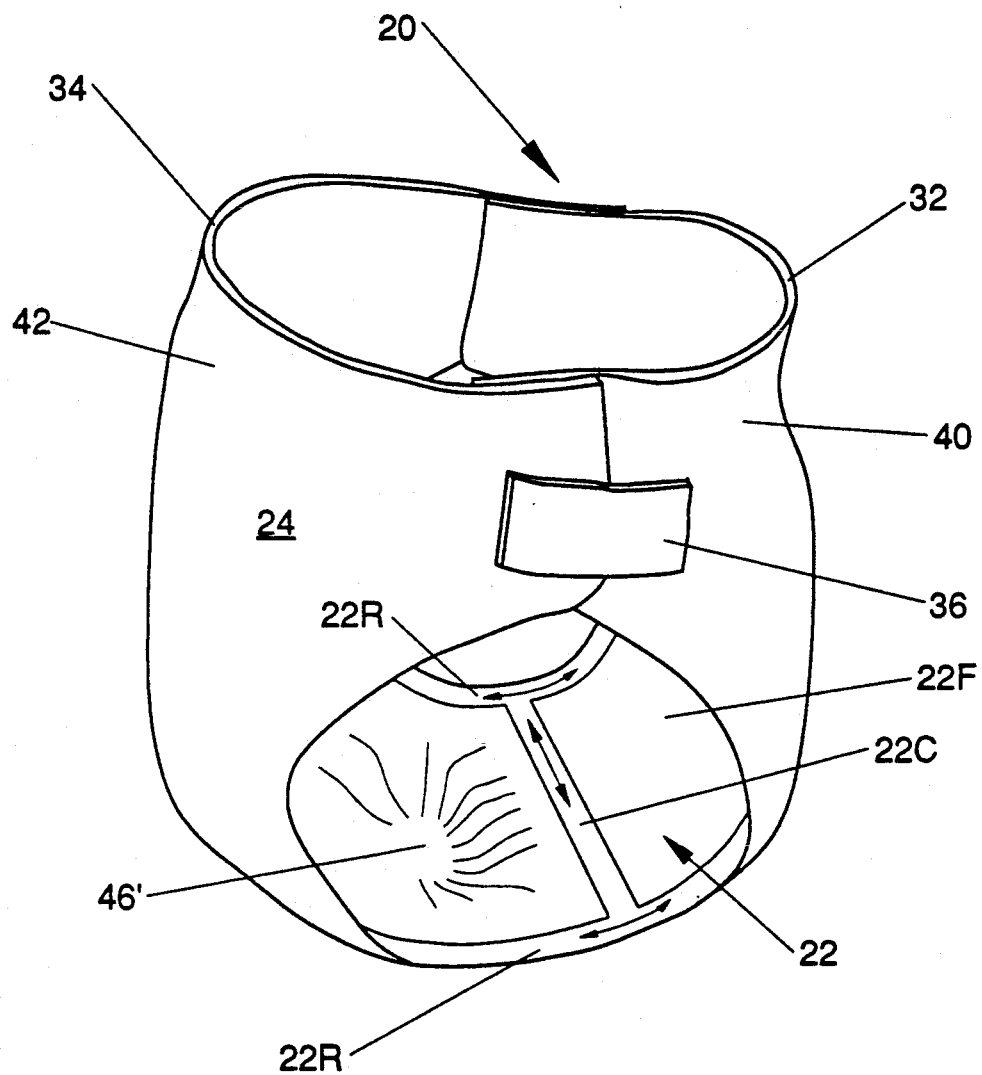
FIG. 6 is a perspective view of the disposable absorbent article of FIG. 5, shown in an in use configuration.

Referring to FIG. 6, this arrangement provides the advantages that a pocket 46' which will accept fecal material may be formed in the rear trisection 22R. Depending upon the relative sizes of the three trisections 22F, 22C, and 22R, the pocket 46' may encompass both the rear and central trisections 22R and 22C. This arrangement is particularly advantageous for embodiments where it is desired to not incorporate an aperture 46 into the topsheet 22. Thus, a topsheet 22 according to the present invention can be constructed without an aperture 46 and advantageously incorporated into a disposable absorbent article 20. In such an embodiment, the core 26 may be provided with longitudinally oriented curvilinear or rectilinear impression lines to predispose the core 26 to assume the shape illustrated in FIG. 6.

Figure 7:
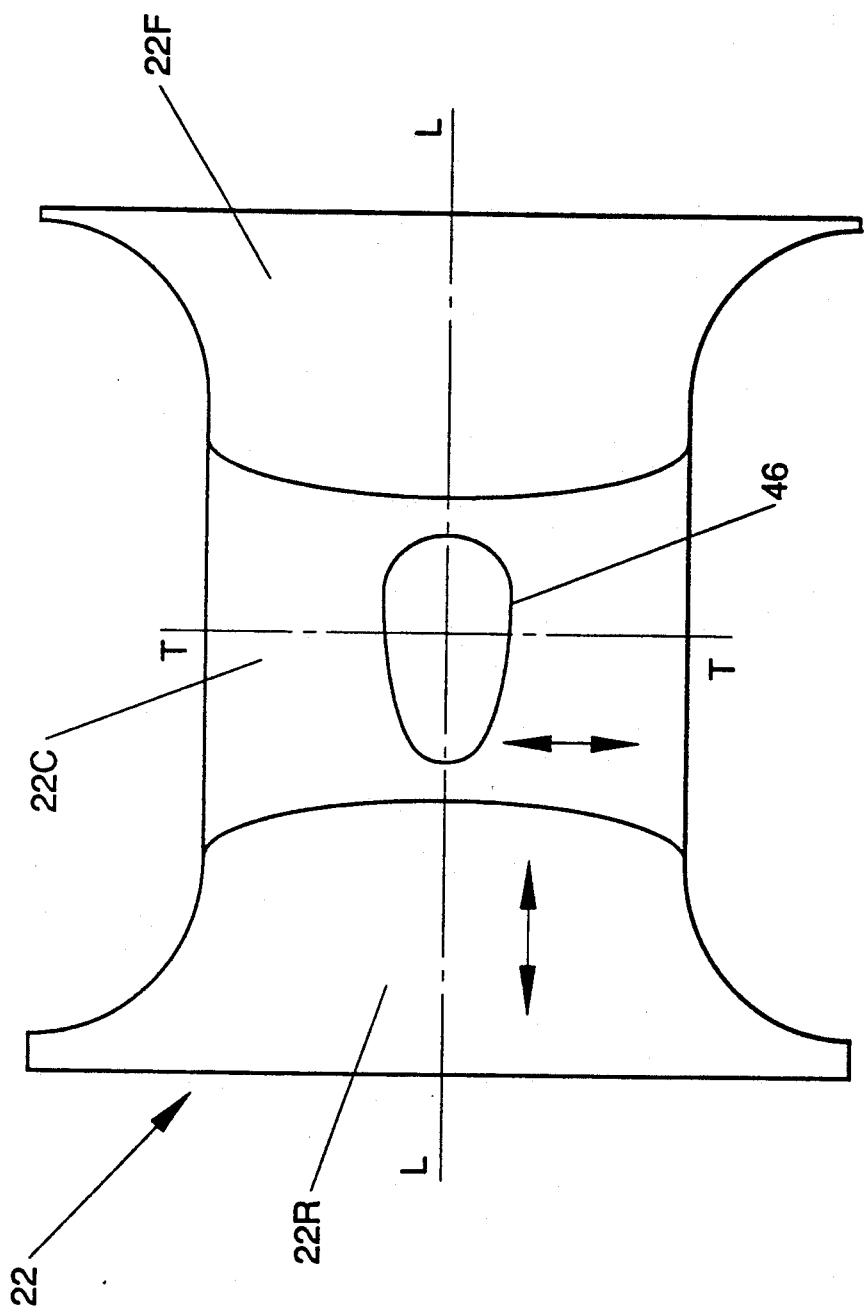
FIG. 7 is a top plan view of a topsheet according to the present invention and having elastic panels with curvilinear borders between the three trisections, which trisections are extensible in the directions of the arrows.

Referring to FIG. 7, in yet another alternative embodiment, the borders between the trisections 22R, 22C, and 22F need not be either rectilinear or parallel. If desired, the borders may be curvilinear and oriented concave towards the respective waist margins 32 and 34. This arrangement provides the advantage, relative to FIG. 1, that the aperture 46 may be formed by a single slit, or otherwise, in the topsheet 22 and reduces the proclivity of the aperture 46 to close in the transverse direction. In another alternative embodiment (not shown), the borders may be curvilinear and oriented convex toward the respective waist margins 32 and 34, and concave towards the transverse axis TT. This arrangement provides the advantage, relative to FIG. 1, that the rear trisection 22R and central trisection 22C more accurately and comfortably conform to the shape of the wearer.

It will be apparent that there are many other variations and permutations possible within the scope of the claimed invention. For example, either the central trisection 22C or the rear trisection 22R may have elastic strands 54 as the means for providing the elastic extensibility and the other trisection 22R or 22C have elastic panels to provide the elastic extensibility. It is not important which particular means for providing the elastic extensibility to the trisection 22R or 22C is selected, but only that the elastic extensibilities (if any) be present in the orientations and positions of the trisections 22F, 22C, and 22R as described above.

If desired, either the central trisection 22C or the rear trisection 22R may have bilateral elastic extensibility. In such an arrangement, the rear trisection 22R has the longitudinally extensibility discussed above and the central trisection 22C has the transverse extensibility discussed above. Additionally, each such trisection 22R and 22C has extensibility in the other principal direction, transverse or longitudinal. It is not necessary that the degree of extensibilities be equal, however, in the longitudinal and transverse directions of a rear or central trisection 22R or 22C having bielastic extensibilities.

It will be apparent to one skilled in the art that the aperture 46 and the central trisection 22C may be sized and arranged so that the aperture 46 is disposed entirely within the central trisection 22C or, alternatively, the aperture 46 may span the central trisection 22C and enter the areas occupied by either the front trisection 22F or the rear trisection 22R. If desired, the aperture 46 and trisections 22F, 22R, and 22C may be sized and disposed so that the aperture 46 spans the central trisection 22C and enters both outboard trisections 22F and 22R.

It will be further apparent that other sections may be disposed among the three trisections 22F, 22C, and 22R in the topsheet 22. For example, a panel having no elastic extensibility may be interposed between the central trisection 22C and either or both of the front and rear trisections 22F and 22R. Alternatively, a panel having no or differently oriented elastic extensibility may be subsumed within a given trisection 22F, 22C, or 22R.

It will be apparent that there are many other variations and combinations of the aforementioned variations, all of which are in the spirit and scope of the claimed invention.

What is claimed is:

1. A topsheet for use in a disposable absorbent article having a front waist margin, a rear waist margin, and a longitudinal axis, said topsheet comprising:
    a front trisection adapted to be juxtaposed with said front waist margin of said disposable absorbent article, said front trisection being generally inelastic;
    a rear trisection adapted to be juxtaposed with said rear waist margin of said disposable absorbent article, said rear waist margin being longitudinally elastically extensible; and
    a central trisection intermediate said front trisection and said rear trisection, at least a portion of said central trisection being transversely elastically extensible, said central trisection being generally H-shaped whereby said central trisection longitudinally extends into at least one of said front trisection and said rear trisection.

2. A topsheet for use in a disposable absorbent article having a front waist margin, a rear waist margin, and a longitudinal axis, said topsheet comprising:
    a front trisection adapted to be juxtaposed with said front waist margin of said disposable absorbent article, said front trisection being generally inelastic;
    a rear trisection adapted to be juxtaposed with said rear waist margin of said disposable absorbent article, said rear waist margin being longitudinally elastically extensible; and
    a central trisection intermediate said front trisection and said rear trisection, said central trisection being transversely elastically extensible, said central trisection longitudinally extending into at least one of said front trisection and said rear trisection,
    wherein said topsheet is unapertured and creates a pocket in said rear trisection for the receipt of fecal material.

3. A topsheet for use in a disposable absorbent article having a front waist margin, a rear waist margin, and a longitudinal axis, said topsheet comprising:
    a front trisection adapted to be juxtaposed with said front waist margin of said disposable absorbent article, said front trisection being generally inelastic;
    a rear trisection adapted to be juxtaposed with said rear waist margin of said disposable absorbent article, said rear waist margin being longitudinally elastically extensible; and
    a central trisection intermediate said front trisection and said rear trisection, said central trisection being transversely elastically extensible, said rear trisection and said central trisection comprising linear elastic strands,
    said topsheet further comprising curvilinear borders between said trisections.

* * * * *

UNITED STATES PATENT AND TRADEMARK OFFICE
CERTIFICATE OF CORRECTION

PATENT NO. : 5,269,775
DATED : DECEMBER 14, 1993
INVENTOR(S) : M. ELAINE FREELAND, PATRICK J. ALLEN

It is certified that error appears in the above-identified patent and that said Letters Patent is hereby corrected as shown below:

Column 6, line 13  delete "No." and insert therefor --Re.--.

Signed and Sealed this

Eighth Day of November, 1994

Attest:

BRUCE LEHMAN

*Attesting Officer*    Commissioner of Patents and Trademarks